United States Patent [19]

Bragulla

[11] Patent Number: 4,528,110
[45] Date of Patent: Jul. 9, 1985

[54] METHOD OF USING ALKYL MONOPHOSPHORIC ACIDS AS GERMICIDAL AGENTS

[75] Inventor: Siegfried Bragulla, Monheim, Fed. Rep. of Germany

[73] Assignee: Henkel Kommanditgesellschaft auf Aktien, Düsseldorf, Fed. Rep. of Germany

[21] Appl. No.: 506,597

[22] Filed: Jun. 22, 1983

[30] Foreign Application Priority Data

Nov. 4, 1982 [DE] Fed. Rep. of Germany ....... 3240688

[51] Int. Cl.$^3$ .......................... C11D 3/48; C11D 3/36
[52] U.S. Cl. .................................... 252/106; 252/142; 252/174.16; 252/174.21; 252/548; 252/DIG. 14; 252/DIG. 17
[58] Field of Search ............. 252/106, 174.16, 174.17, 252/142, DIG. 17; 424/198; 254/DIG. 14

[56] References Cited

U.S. PATENT DOCUMENTS

| 2,765,279 | 10/1956 | Nüsslein | 252/117 |
| 3,312,623 | 4/1967 | Fitch et al. | 252/106 |
| 3,506,579 | 4/1970 | Guttmann et al. | 252/107 |
| 3,671,644 | 6/1972 | Irani et al. | 424/346 |
| 3,923,678 | 12/1975 | Kleiner et al. | 252/174.16 |
| 3,956,199 | 5/1976 | Dawson et al. | 252/545 |

FOREIGN PATENT DOCUMENTS

| 480436 | 5/1974 | Australia. |
| 27083 | 4/1981 | European Pat. Off. . |
| 2327311 | 6/1977 | France. |

Primary Examiner—Prince E. Willis
Attorney, Agent, or Firm—Hammond & Littell, Weissenberger & Dippert

[57] ABSTRACT

This invention is directed to germicidal compositions comprising a germicidally effective amount of at least one alkyl monophosphonic acid having from 4 to 12 carbon atoms in the alkyl chain in admixture with one or more surfactants in acidic solution and to the use of such compositions in disinfecting surfaces.

10 Claims, No Drawings

METHOD OF USING ALKYL MONOPHOSPHORIC ACIDS AS GERMICIDAL AGENTS

FIELD OF THE INVENTION

This invention is directed to novel germicidal agents. More particularly, this invention is directed to the use of certain alkyl monophosphonic acids as germicidal agents in acidic solutions.

BACKGROUND OF THE INVENTION

Various substances are already known as disinfectants in acidic solutions, including, for example, quaternary ammonium compounds, halogen carboxylic acids, and iodine. Unfortunately, these known substances have disadvantages with regard to practical application. For example, quaternary ammonium compounds foam excessively. The foam has to be reduced by use of large quantities of antifoaming agents, which very often impairs the disinfecting effect. In addition, quaternary ammonium compounds cannot be mixed with anionic surfactants, which in turn have a very good degreasing effect.

In acidic cleaners, halogen carboxylic acids, such as, for example, iodoacetic, chloroacetic, or bromoacetic acid, lead to the precipitation of protein which is deposited as a coating on the surfaces to be cleaned or can block the spray nozzles in the cleaning system. Moreover, the halogen carboxylic acids mentioned are not safe to handle because they are highly corrosive. Their relatively high toxicity is another disadvantage so far as their use in ready-made cleaners is concerned.

OBJECTS OF THE INVENTION

It is an object of the invention to provide novel germicidal agents.

It is also an object of the invention to provide a method of using alkyl monophosphonic acids as germicidal agents.

It is a further object of the invention to provide disinfecting agents which, in addition to a broad bacteriological spectrum, are capable of rapidly killing off bacteria when used in low concentrations in acidic cleaners.

These and other objects of the invention will become more apparent in the discussion below.

DETAILED DESCRIPTION OF THE INVENTION

According to the invention, alkyl monophosphonic acids having from 4 to 12, preferably from 8 to 10, carbon atoms in the alkyl chain, in admixture with surfactants, are useful as germicidal agents in acidic solutions. One or more of the alkyl monophosphonic acids are present in an acidic solution in an amount of from about 0.01 to 0.5 grams/liter, preferably from about 0.02 to 0.2 grams/liter, based upon the total volume of the solution, which corresponds to a concentration of from about 10 to 500 ppm, preferably from about 20 to 200 ppm.

The surfactants used may be anionic or, preferably, nonionic, and mixtures of different surfactants may also be used. However, it is best, particularly with regard to undesirable foaming, to use nonionic surfactants such as adducts of ethylene oxide and/or propylene oxide onto fatty alcohols, fatty amines, or fatty acids containing from 12 to 18 carbon atoms in the alkyl chain or onto alkyl phenols containing from 6 to 15 carbon atoms in the alkyl chain. The mixing ratio in percents by weight of alkyl monophosphonic acids to surfactants may be in the range of from about 1:1 to 1:5, although a ratio of about 1:4 is preferred.

In addition to the surfactants, which inter alia also improve the solubility of the alkyl monophosphonic acids, it is possible to add other solubilizers, or solution promoters. Examples of such solubilizers include cumene sulfonate and monohydric or dihydric short-chain alcohols, such as ethanol, propanol, glycol, and butyl diglycol.

The concentration of acid in the acidic solutions used may be in the range of from about 0.1 to 2% by weight, preferably from about 0.5 to 0.6% by weight, based upon the total weight of acidic solution. Suitable acids include HCl, $H_2SO_4$, $HNO_3$, amidosulfonic acid, and, in particular, phosphoric acid.

Alkyl-1-phosphonic acids are preferred according to the invention, although octane-1-phosphonic acid and decane-1-phosphonic acid have proven to be the best disinfecting agents. They do not foam, are dermatologically and toxicologically safe, and have a distinct germicidal effect in acid solutions even at low temperatures.

Germicidal agents containing alkyl monophosphonic acids according to the invention can be effectively used to disinfect virtually any non-porous surface. Examples of such surfaces include metal and enamel surfaces and, preferably, glass or plastic surfaces.

The following examples are intended to illustrate the invention and should not be construed as limiting it thereto.

EXAMPLES

Example 1

The germicidal effect of octane-1-phosphonic acid in various concentrations in phosphoric acid solution was tested. The respective solutions are identified as Solutions A to E in the following table:

TABLE 1

| Components (% by weight): | Solution: | | | | |
| --- | --- | --- | --- | --- | --- |
| | A | B | C | D | E |
| (a) octane-1-phosphonic acid | 0.0 | 0.3 | 0.5 | 1.0 | 1.3 |
| (b) adduct of 8 mols of EO onto nonyl phenol | 2.0 | 2.0 | 2.0 | 2.0 | 2.0 |
| (c) adduct of 5 mols of EO and 4 mols of PO onto $C_{12}$–$C_{14}$-fatty alcohol | 4.0 | 4.0 | 4.0 | 4.0 | 4.0 |
| (d) phosphoric acid, 100% | 37.5 | 37.5 | 37.5 | 37.5 | 37.5 |
| (e) condensed water | 56.5 | 56.2 | 56.0 | 55.5 | 55.2 |

EO = ethylene oxide
PO = propylene oxide

The suspension test developed by the "Deutschen Landwirtschafts-Gesellschaft e.V." (DLG) was used both in this and the following examples. The suspension test for disinfectants is carried out as follows: The agent is tested for its effectiveness against the bacterial strains indicated in Table 2 below. To this end, the agent to be tested is dissolved in standardized hard water [total hardness: 15° dH (dh=deutsch Härte=German Hardness)]. To check bactericidal activity, quantities of 0.1 ml of the bacterial suspension are added to 10 ml of disinfectant solution, and the destruction time in minutes is determined at the test temperature of 20° C.

The destruction times are shown in the following table:

TABLE 2

Destruction time (minutes) at 20° C.
(DLG suspension test); water hardness = 15° dH

| Test Strain: | Solution: | | | | | | | | | |
|---|---|---|---|---|---|---|---|---|---|---|
| | A | | B | | C | | D | | E | |
| | Concentration (% by wt.): | | | | | | | | | |
| | 0.5 | 1 | 0.5 | 1 | 0.5 | 1 | 0.5 | 1 | 0.5 | 1 |
| Staphylococcus aureus | 60 | 20 | 5 | 1 | 1 | 1 | 1 | 1 | 1 | 1 |
| Streptococcus faecalis | 40 | 40 | 20 | 10 | 10 | 5 | 10 | 2.5 | 2.5 | 1 |
| Pseudomonas fluorescens | 20 | 10 | 10 | 2.5 | 10 | 10 | 2.5 | 2.5 | 5 | 2.5 |
| Klebsiella aerogenes | 10 | 10 | 5 | 5 | 2.5 | 2.5 | 5 | 5 | 5 | 5 |

Example 2

The increase in germicidal activity was tested in the same manner as in Example 1. The composition of the germicidal cleaning solutions was as follows:

TABLE 3

| Components (% by weight): | Solution: | |
|---|---|---|
| | F | G |
| (a) phosphoric acid, 100% | 45.0 | 45.0 |
| (b) adduct of 5 mols of EO onto oleyl alcohol | 0.4 | 0.4 |
| (c) adduct of 9 mols of EO and 10 mols of PO onto nonyl phenol | 3.5 | 3.5 |
| (d) adduct of 12 mols of EO onto nonyl phenol | 1.0 | 1.0 |
| (e) octane-1-phosphonic acid | 0.0 | 1.3 |
| (e) condensed water | 50.1 | 48.8 |

The destruction times are shown in the following table:

TABLE 4

Destruction times (minutes) at 20° C.
(DLG suspension test); water hardness = 15° dH

| Solution: | F | | G | |
|---|---|---|---|---|
| Concentration (% by wt.): | 0.5 | 1 | 0.5 | 1 |
| Test strain: | | | | |
| Staphylococcus aureus | 60 | 60 | 2.5 | 1 |
| Streptococcus faecalis | 40 | 40 | 5 | 1 |
| Pseudomonas fluorescens | 20 | 1 | 5 | 1 |
| Klebsiella aerogenes | 10 | 10 | 2.5 | 2.5 |

Example 3

The germicidal activity of alkyl-1-phosphonic acids containing a $C_4$–$C_{12}$-alkyl radical was tested in cleaning solutions having the compositions shown in Table 5. The results, in destruction time, are set forth in Table 6 with regard to the alkyl monophosphonic acids contained in the solutions.

TABLE 5

| Components (% by weight): | Formulation: | | | | | |
|---|---|---|---|---|---|---|
| | 1 | 2 | 3 | 4 | 5 | Control |
| (a) butane-1-phosphonic acid | 1.0 | — | — | — | — | — |
| (b) hexane-1-phosphonic acid | — | 1.0 | — | — | — | — |
| (c) decane-1-phosphonic acid | — | — | 1.0 | — | — | — |
| (d) dodecane-1-phosphonic acid | — | — | — | 1.0 | — | — |
| (e) octane-1-phosphonic acid | — | — | — | — | 1.0 | — |
| (f) no phosphonic acid added | — | — | — | — | — | 0 |
| (g) adduct of 12 mols of EO onto nonyl phenol | 4.0 | 4.0 | 4.0 | 4.0 | 4.0 | 4.0 |
| (h) phosphoric acid, 100% | 37.5 | 37.5 | 37.5 | 37.5 | 37.5 | 37.5 |
| (i) condensed water | 57.5 | 57.5 | 57.5 | 57.5 | 57.5 | 58.5 |

TABLE 6

| Test strain: | Formulation: | | | | | | | | | | Control | |
|---|---|---|---|---|---|---|---|---|---|---|---|---|
| | 1 | | 2 | | 3 | | 4 | | 5 | | | |
| | Concentration of the solution (% by wt.): | | | | | | | | | | | |
| | 0.5 | 1 | 0.5 | 1 | 0.5 | 1 | 0.5 | 1 | 0.5 | 1 | 0.5 | 1 |
| Staphylococcus aureus | 40 | 5 | 40 | 5 | 1 | 1 | 10 | 10 | 2.5 | 2.5 | 20 | 20 |
| Streptococcus faecalis | 20 | 10 | 20 | 10 | 1 | 1 | 20 | 10 | 5 | 2.5 | 20 | 20 |
| Pseudomonas fluorescens | 2.5 | 1 | 2.5 | 2.5 | 1 | 1 | 5 | 2.5 | 5 | 2.5 | 10 | 2.5 |
| Klebsiella aerogenes | 5 | 2.5 | 2.5 | 1 | 2.5 | 2.5 | 5 | 1 | 5 | 2.5 | 2.5 | 1 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A method of disinfecting a surface which comprises applying thereto an effective amount of a germicidal composition which comprises a germicidally effective amount of at least one alkyl monophosphonic acid having from 4 to 12 carbon atoms in the alkyl chain in admixture with one or more anionic or nonionic surfactants in solution, which solution contains from about 0.1 to 2 percent by weight of an acid selected from the group consisting of HCl, $H_2SO_4$, $HNO_3$, amidosulfonic acid and phosphoric acid.

2. The method of disinfecting a surface according to claim 1, wherein the surfactants utilized are nonionic.

3. The method of disinfecting a surface according to claim 2, wherein the surfactants are selected from the group comprising adducts of ethylene oxide and/or propylene oxide onto fatty alcohols, fatty amines, or fatty acids containing from 12 to 18 carbon atoms in the alkyl chain.

4. The method of claim 1, wherein the alkyl monophosphonic acid has from 8 to 10 carbon atoms in the alkyl chain.

5. The method of claim 1, wherein the weight ratio of alkyl monophosphonic acid to surfactant is from about 1:1 to 1:5.

6. The method of claim 1, wherein the concentration of alkyl monophosphonic acid is from about 0.01 to 0.5 grams/liter.

7. The method of claim 6, wherein the concentration is from about 0.02 to 0.2 grams/liter.

8. The method of claim 1, wherein the alkyl monophosphonic acid is an alkyl-1-phosphonic acid or a mixture thereof.

9. The method of claim 8, wherein the alkyl monophosphonic acid is octane-1-phosphonic acid, decane-1-phosphonic acid, or a mixture thereof.

10. The method of claim 1 which contains from about 0.5 to 0.6% by weight of said acid.

* * * * *